(12) United States Patent
Hariharan et al.

(10) Patent No.: US 8,378,149 B2
(45) Date of Patent: Feb. 19, 2013

(54) PROCESS FOR PRODUCTION OF 1,2,2,2-TETRAFLUOROETHYL DIFLUOROMETHYL ETHER (DESFLURANE)

(75) Inventors: Sivaramakrishnan Hariharan, Mumbai (IN); Owen Chambers, Filton (GB); Abhay Atmaram Upare, Mumbai (IN); Damodharan Satagopan, Basheerbagh (IN)

(73) Assignee: Piramal Enterprises Limited, Mumbai, Maharashtra (IN)

( * ) Notice: Subject to any disclaimer, the term of this patent is extended or adjusted under 35 U.S.C. 154(b) by 355 days.

(21) Appl. No.: 12/668,984

(22) PCT Filed: Jul. 11, 2008

(86) PCT No.: PCT/IB2008/052801
§ 371 (c)(1),
(2), (4) Date: Jan. 13, 2010

(87) PCT Pub. No.: WO2009/010908
PCT Pub. Date: Jan. 22, 2009

(65) Prior Publication Data
US 2010/0185020 A1    Jul. 22, 2010

(30) Foreign Application Priority Data
Jul. 13, 2007   (IN) ................... 1343/MUM/2007

(51) Int. Cl.
*C07C 41/22*   (2006.01)
(52) U.S. Cl. ........................... 568/683; 568/682
(58) Field of Classification Search ............ None
See application file for complete search history.

(56) References Cited

U.S. PATENT DOCUMENTS

| | | | |
|---|---|---|---|
| 2,478,362 A | 8/1949 | Benning | |
| 3,535,388 A | 10/1970 | Terrell | |
| 3,897,502 A | 7/1975 | Russell et al. | |
| 4,079,089 A * | 3/1978 | Klauke | 570/145 |
| 4,436,942 A | 3/1984 | Rader et al. | |
| 4,762,856 A | 8/1988 | Terrell | |
| 5,015,781 A | 5/1991 | Robin et al. | |
| 5,026,924 A | 6/1991 | Cicco | |
| 6,054,626 A | 4/2000 | Chambers et al. | |
| 6,074,985 A | 6/2000 | Elsheikh et al. | |
| 6,270,742 B1 | 8/2001 | Ewing et al. | |
| 6,608,155 B2 | 8/2003 | Babcock et al. | |
| 6,635,231 B2 | 10/2003 | Smith et al. | |
| 6,800,786 B1 | 10/2004 | Rozov et al. | |
| 2006/0205983 A1 | 9/2006 | Terrell et al. | |

FOREIGN PATENT DOCUMENTS

| | | |
|---|---|---|
| DE | 23 61 058 | 6/1975 |
| EP | 0 341 005 B1 | 11/1989 |
| GB | 2 219 292 A | 5/1989 |
| WO | WO 2006/055749 A1 | 5/2006 |
| WO | WO 2006/076324 A2 | 7/2006 |
| WO | WO 2006/121479 A1 | 11/2006 |

OTHER PUBLICATIONS

Mazej et al., "Synthesis of arsenic pentafluoride by static fluorination of As2O3 in a closed system," *Journal of Fluorine Chemistry* (2005) 126: 1432-1434.
Yang et al., "Investigation into antimony pentafluoride-based catalyst in preparing organo-fluorine compounds," *Journal of Molecular Catalysis A: Chemical* (2005) 233: 99-104.

* cited by examiner

*Primary Examiner* — Rosalynd Keys
(74) *Attorney, Agent, or Firm* — Merchant & Gould P.C.

(57) ABSTRACT

The present invention provides a continuous process for the production of 1,2,2,2-tetrafluoroethyl difluoromethyl ether (desflurane) which comprises feeding continuously optimum molar quantities of 1-chloro-2,2,2-trifluoroethyl difluoromethyl ether ($CF_3CHClOCHF_2$, Isoflurane) and anhydrous hydrogen fluoride, in a reactor in the vapor phase over a fluorination catalyst system comprising a metal pentahalide absorbed on a supporting substrate at a temperature ranging from 100° C. to 180° C., and separating 1,2,2,2-tetrafluoroethyl difluoromethyl ether (desflurane) continuously from the reactor. The process of the present invention enables continuous removal of desflurane product thereby minimizing co-production of byproducts and resulting in high conversion efficiency and yield of desflurane.

14 Claims, No Drawings

US 8,378,149 B2

PROCESS FOR PRODUCTION OF 1,2,2,2-TETRAFLUOROETHYL DIFLUOROMETHYL ETHER (DESFLURANE)

This application is a National Stage Application of PCT/IB2008/052801, filed Jul. 11, 2008, which claims benefit of Ser. No. 1343/MUM/2007, filed Jul. 13, 2007 in India and which applications are incorporated herein by reference. To the extent appropriate, a claim of priority is made to each of the above disclosed applications.

FIELD OF INVENTION

The present invention relates to a process for the preparation of fluorinated ethers, particularly, 1,2,2,2-tetrafluoroethyl difluoromethyl ether ($CF_3CHFOCHF_2$), called desflurane which is known to have valuable anaesthetic properties and is especially useful as an inhalation anaesthetic. More particularly, the invention is directed to a continuous vapour phase process for the production of desflurane. The present invention provides a simple, cost-effective, efficient and continuous process for the production of desflurane.

BACKGROUND OF THE INVENTION

The compound 1,2,2,2-tetrafluoroethyl difluoromethyl ether ($CF_3CHFOCHF_2$), also known as desflurane, is an important inhalation anaesthetic. It is considered to be particularly safe due to its very low level of metabolism within the human body and is also particularly suited for administration for out patient procedures due to the rapid rate of patient recovery from anaesthesia.

There are several known methods for the preparation of desflurane. A process described in U.S. Pat. No. 3,897,502 for the preparation of desflurane involves direct fluorination of the ether, $CF_3$—$CH_2$—$OCHF_2$ (2-difluoromethoxy-1,1,1-trifluoroethane) using elemental fluorine as the fluorinating agent. The reaction is carried out in a fluorinated solvent (Freon E3) using a mixture of 20% fluorine gas in argon, at $-20°$ C. to $-25°$ C. and over a long time to control the strong exothermic process. Due to the slow reaction time, low reaction temperature and the use of expensive and hazardous elemental fluorine in this process, it would be difficult to scale it up for commercial purposes. U.S. Pat. No. 6,054,626 partly addresses drawbacks associated with this process by disclosing a vapour phase process for producing desflurane. This process involves contacting CF3—$CH_2$—$OCHF_2$ (2-difluoromethoxy-1,1,1-trifluoroethane) in the vapour phase with a solid transition metal fluoride, preferably cobalt trifluoride as the fluorinating agent. The transition metal fluoride fluorinating agent can be regenerated in situ during the reaction by passing fluorine into the reaction zone such that cobalt trifluoride acts as a fluorine carrier. However, this process suffers from drawbacks such as relatively low yields of desflurane, formation of significant amounts of other polyfluorinated ether isomers and by-products. Moreover, this process also involves use of expensive and hazardous elemental fluorine.

The preparation of desflurane using isoflurane as the starting material and alkali metal fluorides as the fluorinating agents have been known. EP Patent No. 341,005B teaches a process for the manufacture of desflurane wherein a chlorofluoro organic ether, especially isoflurane is reacted with sodium fluoride or potassium fluoride at a temperature of 278° C. and an elevated pressure (500 psi) in the absence of a solvent. The process has to be operated at very high temperature and elevated pressure for a long period of time, resulting in significant capital cost. UK Patent Application No. GB 2,219,292A discloses a process for the manufacture of desflurane wherein isoflurane is reacted with an alkali metal fluoride (sodium fluoride, cesium fluoride, potassium fluoride) in an aprotic polar solvent (sulpholane) in the presence of a phase transfer catalyst (tetramethylammonium chloride) at a temperature of 210° C. This process also operates at a very high temperature. Moreover, both these processes are essentially batch processes.

An alternative method for producing desflurane from isoflurane using bromine trifluoride as a fluorinating agent has been disclosed in U.S. Pat. Nos. 4,762,856 and 5,015,781. Although the process gives a good yield and requires only a short reaction time, it employs bromine trifluoride, which poses significant handling problems and is expensive and therefore, not suitable for commercial manufacture.

Ger. Offen. DE 2361058 relates to a method of producing desflurane which involves initially chlorinating $CF_3$—CHF—O—$CH_3$ (1,2,2,2-tetrafluoroethyl methyl ether) to $CF_3$—CHF—O—$CHCl_2$ (1,2,2,2-tetrafluoroethyl dichloromethyl ether) and reacting the resulting chlorinated ether with anhydrous hydrogen fluoride using antimony pentachloride as a catalyst. This process suffers from the drawback that it may not be suitable for industrial scale up due to the lack of accessibility of the initial starting material. Moreover, this is a complex multistep process.

U.S. Pat. No. 5,026,924 describes a method of preparing desflurane by reacting isoflurane with excess hydrogen fluoride in the presence of an antimony pentachloride catalyst, alone or in combination with a small amount of antimony trichloride at relatively low temperature range of $-10°$ C. to 30° C. This process suffers from the disadvantage that it is necessary to use a substantial molar excess of hydrogen fluoride in order to achieve acceptable yields and conversions. The use of excess fluorinating agent adds to the cost of preparation and necessitates the removal of excess hydrogen fluoride. U.S. Pat. No. 6,800,786 teaches a process for the manufacture of desflurane, which involves reacting isoflurane with optimum quantities of anhydrous hydrogen fluoride in presence of optimum quantity of antimony pentachloride to minimise the level of by-products formed and to increase the yield of desflurane. However, this process also results in difficult to separate by-products ultimately resulting in reduced yield of desflurane. A more recent International Patent Publication No. WO2006/055749 teaches the use of antimony pentafluoride instead of antimony pentachloride or mixed antimony chlorofluoride catalysts for reacting isoflurane and anhydrous HF while avoiding the necessity of using a molar excess of hydrogen fluoride. The reaction is carried out in a similar manner to the processes involving use of antimony pentachloride, but a lower molar ratio of hydrogen fluoride to isoflurane have been used. This process also claimed the benefits of a lower production of troublesome by-products. Although both processes employ antimony pentachloride or antimony pentafluoride catalysts which might improve the overall reaction conversion and yield as compared to using anhydrous HF alone, the reaction is either a batch or semi-continuous process involving disposal of the expensive catalyst after each batch.

Finally, a vapour phase process has been described in International Patent Publication No. WO 2006/076324 in which an isoflurane and hydrogen fluoride mixture in the vapour phase is passed over a chromia catalyst bed at 140° C. or 170° C. However, at the higher temperature a considerable amount of cleavage of the carbon-oxygen bond occurred to give about 10% of fragmentation products. At the lower temperature very little fragmentation occurred, but the conversion was only about 50%. This process hence has the disadvantage of a low conversion rate or a reduced yield due to fragmentation. Although the process is continuous it requires a higher hydrogen fluoride: isoflurane molar ratio resulting in higher hydrogen fluoride recycle or loss of hydrogen fluoride. Hence, there is a need to develop a vapour phase process which is efficient and can substantially eliminate the drawbacks of the existing processes.

The inventors of this invention have made possible a continuous vapor phase fluorination process for the preparation of desflurane by reacting optimum concentrations of isoflurane and a fluorinating agent such as anhydrous HF in presence of an efficient and easy to handle flourination catalyst. The vapor phase process minimizes the corrosion associated with liquid-phase catalytic fluorination especially those employing antimony halide catalysts. The process of the present invention enables continuous removal of desflurane product thereby minimizing co-production of byproducts and resulting in high conversion efficiency and yield of desflurane.

OBJECTS OF THE INVENTION

Thus, the main object of the present invention is to provide a continuous vapour phase process for the production of 1,2,2,2-tetrafluoroethyl difluoromethyl ether ($CF_3CHFOCHF_2$, desflurane). Another object of the invention is to provide a continuous vapour phase process for the production of 1,2,2,2-tetrafluoroethyl difluoromethyl ether ($CF_3CHFOCHF_2$, Desflurane) with high conversion efficiency.

Another object of the invention is to provide a continuous vapour phase fluorination process for the production of 1,2,2,2-tetrafluoroethyl difluoromethyl ether ($CF_3CHFOCHF_2$, desflurane) with high yield and purity.

Yet another object of the invention is to provide a continuous vapour phase process for the production of 1,2,2,2-tetrafluoroethyl difluoromethyl ether ($CF_3CHFOCHF_2$, desflurane) by employing an efficient fluorination catalyst system having a relatively higher catalytic activity.

Yet another further object of the invention is to provide a continuous process for the production of 1,2,2,2-tetrafluoroethyl difluoromethyl ether ($CF_3CHFOCHF_2$, Desflurane) which comprises feeding continuously optimum molar quantities of 1-chloro-2,2,2-trifluoroethyl difluoromethyl ether ($CF_3CHClOCHF_2$, Isoflurane) and anhydrous hydrogen fluoride, in a reactor in the vapour phase over a fluorination catalyst system comprising a metal pentahalide absorbed on a supporting substrate at a temperature ranging from 100° C. to 180° C., and separating 1,2,2,2-tetrafluoroethyl difluoromethyl ether ($CF_3CHFOCHF_2$, desflurane) continuously from the reactor.

STATEMENT OF INVENTION

In accordance with the first aspect of this invention, there is provided a process for the production of 1,2,2,2-tetrafluoroethyl difluoromethyl ether ($CF_3CHFOCHF_2$, desflurane) comprising feeding continuously to a reactor, a feed mixture consisting of 1-chloro-2,2,2-trifluoroethyl difluoromethyl ether ($CF_3CHClOCHF_2$, Isoflurane) and anhydrous hydrogen fluoride, in the vapour phase and in presence of a fluorination catalyst system comprising a metal pentahalide absorbed on a supporting substrate at a temperature ranging from 100° C. to 180° C., and recovering 1,2,2,2-tetrafluoroethyl difluoromethyl ether (desflurane) continuously from the reactor.

In accordance with another aspect of the invention, the vapour phase reaction is carried out over a fluorination catalyst system consisting of one or more metal pentahalides absorbed on a supporting substrate.

In accordance with yet another aspect of the invention, the process for the production of desflurane is operated continuously.

DESCRIPTION OF THE INVENTION

The present invention is directed to an improved process for the production of 1,2,2,2-tetrafluoroethyl difluoromethyl ether (desflurane) comprising passing to a reactor, a feed mixture consisting of 1-chloro-2,2,2-trifluoroethyl difluoromethyl ether (isoflurane) and anhydrous hydrogen fluoride in optimum molar quantities, in the vapour phase over a fluorination catalyst system consisting essentially of a metal pentahalide absorbed onto a supporting substrate, at a temperature ranging from 100° C.-180° C. to produce 1,2,2,2-tetrafluoroethyl difluoromethyl ether (desflurane) and recovering desflurane from the reaction feed continuously.

The starting material, 1-chloro-2,2,2-trifluoroethyl difluoromethyl ether (isoflurane) used in the process of the present invention is commercially available with high purity and relatively very little volatile components. Isoflurane can also be synthesised as per the method described in Terrell et al., U.S. Pat. No. 3,535,388 incorporated herein by reference. Isoflurane employed in the process has a boiling point of 48.5° C. and hence, can be readily vapourised by heating so that it can be fed as a vapour to the reactor.

Many of the commercial grades of hydrogen fluoride that are available are found to be acceptable in this process. As anhydrous hydrogen fluoride has a boiling point of 19° C., it can also be easily vaporized and fed to the reactor.

Generally, it is preferred that the starting materials, isoflurane and hydrogen fluoride are moisture-free, as any water in the vapour phase reaction can both impair and degrade the fluorination catalyst and also cause the formation of undesirable by-products, which might pose difficulty in subsequent separation stages and lower the yield of desflurane.

The fluorination catalyst system employed in the process comprises a metal pentahalide absorbed onto a supporting substrate. The metal pentahalide is selected from a group consisting of antimony pentahalides, arsenic pentahalides, tantalum pentahalides and niobium pentahalides or mixtures thereof. When arsenic pentahalide is selected as the catalyst then it is preferred that arsenic pentafluoride is used. Antimony pentahalides, tantalum pentahalides and niobium pentahalides are available commercially from speciality chemical manufacturers and in good quality. Arsenic pentafluoride is more difficult to obtain and may have to be synthesised by methods described in the literature (Journal Of Fluorine Chemistry; Vol. 126, Issues 9-10 Oct. 2005 Pages 1432-1434; U.S. Pat. No. 6,635,231).

The metal pentahalides should be preferably in anhydrous form because presence of moisture may impair the conversion, yield and purity of the end product.

In one embodiment of the invention, the metal pentahalide contained in the fluorination catalyst system is selected from antimony pentachloride and antimony pentafluoride.

In another embodiment of the invention, the supporting substrate in the fluorination catalyst system is selected from carbon, preferably activated carbon, and alumina, which are readily available commercially. The activated carbon support is essentially a moisture-free activated carbon. It is not critical to the process of the present invention that the activated carbon be pretreated with a fluorinating agent, however it could be pretreated with a fluorinating agent such as hydrogen fluoride as described in the U.S. Pat. No. 6,074,985 incorporated herein by reference. An example of the type of preparation of such a supported catalyst is illustrated in Journal of molecular catalysis 2005; 233(99-104) incorporated herein by reference.

Two types of alumina are available for use in the vapour phase process, alpha alumina and gamma alumina (also known as activated alumina). The activated alumina has a higher surface area and therefore higher catalytic activity but could also produce water, limiting the life span of the fluorination catalyst. Particularly if gamma alumina is used, then this is preferably treated with HF, prior to its use as a support, to fluorinate exposed hydroxy groups and thus prevent the formation of water which would degrade the catalyst. Gamma alumina can be pretreated with hydrogen fluoride by the process described in U.S. Pat. No. 4,436,942, which is incorporated herein by reference.

The supporting substrate employed in the process of the present invention, may be subjected to additional drying to eliminate any absorbed water. These drying procedures can involve either passing a non-active gas (e.g. nitrogen) over the heated support or else heating under a vacuum.

The fluorination catalyst system may be prepared by dissolving the required amount of metal pentahalide in dried isoflurane, desflurane or other suitable solvent. The concentration of the metal pentahalide in the solvent is not critical but typically it can be about 15% w/w. The previously dried supporting substrate is added to the metal pentahalide solution in presence of nitrogen such that the metal pentahalide gets absorbed onto the substrate to produce supported fluorination catalyst system. In the fluorination catalyst system, the concentration of metal pentahalide on the substrate is in the range from 0.5 to 4.0 mmol/g, preferably from 0.5 to 2.5 mmol/g, most preferably from 1.0 to 2.0 mmol/g.

The supported fluorination catalyst system, with the solvent, can be directly loaded to the reactor. However, it is preferred that a stream of dry gas, generally nitrogen is passed over the catalyst system to remove any solvent, prior to employing the catalyst in the vapour phase process. The fluorination catalyst system can be preferably loaded into the vapour phase reactor under a nitrogen atmosphere. The fluorination catalyst system in the reactor can be in the form of a packed bed, a mechanically agitated bed or a fluidised bed.

The supported catalyst is then pretreated with gaseous anhydrous hydrogen fluoride for about 4 to 16 hours, with the temperature being raised in stages from ambient temperature to 130° C. Typically, each stage is about 2-4 hours, the first stage at about 50° C., second stage at about 70° C. and the final stage at 100° C.-130° C. The pretreatment and heating process substantially lowers the risk of the degradation of the supported catalysts comprising metal pentafluorides. For metal pentachlorides, an extra initial low temperature stage at 30° C.-35° C. for 3 to 4 hours is preferred.

The supported flourination catalyst employed in this vapour phase process demonstrates excellent catalytic activity and overcomes drawbacks such as having to dispose of large amounts of corrosive and toxic materials associated with unsupported antimony pentafluoride or antimony pentachloride catalysts employed in catalytic fluorination reactions.

In one embodiment of the invention, the gaseous 1-chloro-2,2,2-trifluoroethyl difluoromethyl ether (isoflurane) and the hydrogen fluoride in the vapour phase can be fed continuously over a packed bed of fluorination catalyst system at a temperature ranging from 100° C.-180° C., preferably at 120° C.-150° C. The reaction can be carried out at an elevated pressure or a reduced pressures or an atmospheric pressure, preferably in the range 0.5-10 bar and more preferably in the range 0.8-4 bar.

In one embodiment of the present invention, the molar equivalent of anhydrous fluoride to 1-chloro-2,2,2-trifluoroethyl difluoromethyl ether (isoflurane) in the reactant feed mixture varies from 0.25:1 to 10:1, preferably 1:1 to 5:1 and most preferably 1.5:1 to 4:1.

The process of the present invention further comprises recovering the product, 1,2,2,2-tetrafluoroethyl difluoromethyl ether (desflurane) continuously from the reactor by condensation and neutralization. The hydrogen chloride (HCl) produced in the vapour phase catalytic fluorination process and relatively insubstantial amount of excess hydrogen fluoride in the reaction feed are then scrubbed out using aqueous sodium hydroxide.

If desired, the exit gases can also be subjected to a high pressure and condensed. The HCl is removed by a distillation method known to person skilled in the art (U.S. Pat. No. 2,478,362). The relatively insubstantial amount of excess hydrogen fluoride in the reaction feed can then be separated from the desflurane, by solvent extraction of the crude desflurane by a process as described in International Patent Application No. WO 2006/121479 or by extraction of hydrogen fluoride by a polar medium by a process as described in U.S. Pat. No. 6,270,742.

The advantages of the process of the present invention can be summed up as follows:

The process produces 1,2,2,2-tetrafluoroethyl difluoromethyl ether (desflurane) of high yield and purity.

The vapour phase process minimizes the corrosion associated with liquid-phase catalytic fluorinations especially those employing antimony halide catalysts and produces 1,2,2,2-tetrafluoroethyl difluoromethyl ether (desflurane) of high yield and purity.

The process employs an efficient and easy to handle fluorination catalyst system minimising by-product formation and improving the product selectivity and yield.

The process employs continuous removal of desflurane product resulting in good conversion efficiency, minimizing energy input, making it industrially scalable and cost effective.

The following examples which fully illustrate the practice of the preferred embodiments of the present invention are intended to be for illustrative purposes only and should not be construed in anyway to limit the scope of this invention.

EXAMPLES

Equipment

The reactor used in the present process consisted of an Inconel tube of 1 inch diameter with a catalyst bed length of 14 inches and total length of about 24 inches. The total volume of catalyst in the reactor was thus 170 ml, after allowing for the thermocouple volume. The thermocouple measured the temperature near the center of the bed.

The starting material, 1-chloro-2,2,2-trifluoroethyl difluoromethyl ether (isoflurane) was fed as a liquid at a controlled rate by a syringe pump and mixed with hydrogen fluoride (HF) vapour. The mixture was then passed to a vapouriser at 70° C.-80° C. The gas mixture was then passed through a preheater zone above the bed at about 110-120° C. The HF was fed as a vapour directly from a cylinder and the feed rate was controlled by a needle valve and monitored with the balance.

The reactor outlet gases from the reactor were cooled and then quenched in aqueous alkali. The desflurane product was then separated by phase separation from the aqueous layer. The crude desflurane product was then analysed by gas-liquid chromatography, using the column specified in the USP monograph (30 Apr. 2007).

Typical Catalyst Preparation

Activated carbon (60 g) was placed in a tubular reactor and heat dried at 180° C. for 8 hours under nitrogen flow of ~100 cc/min. The activated carbon obtained was an extrude of diameter 1.5 to 2 mm, length 3-4 mm and density 0.4-0.45. The activated carbon was then unloaded from the reactor under nitrogen flow in a self-sealing plastic bag, while keeping nitrogen flow inside the bag. The bag was then closed.

Previously cooled isoflurane (100 g) was added to a nitrogen purged teflon assembly of 500 ml capacity followed by charging an appropriate amount of metal pentahalide solution depending on the loading required. The assembly was then immediately charged with an activated dried carbon.

The reactor was purged with nitrogen for about 1 hour to remove any solvent. An HF flow was then commenced (3-4 g/hr), the nitrogen flow was discontinued after co-feeding with HF for 1 hour. For the metal pentachloride, there was an initial 3-4 hours treatment at 30-35° C. Both the metal pentafluorides and the metal pentachlorides were then heated to 50-70° C. for 3 to 4 hours, temperature raised to 100-120° C. and the HF feed continued for a further 1 to 3 hours. The temperature was then raised further to desired reaction temperature, before commencing the isoflurane feed for vapour phase catalytic fluorination process.

Example 1

The fluorination catalyst was prepared, charged, conditioned and heated to the reaction temperature (150° C.) as described above. The metal pentahalide employed in the process was antimony pentachloride in molar equivalents of 1.1 mmol/g. The supporting substrate employed was the activated carbon. The pressure of the system was 0-0.2 bar.

Isoflurane was fed continuously as a vapour at a rate of 22.3 g/hr and anhydrous HF vapour was fed at a rate of 4.6 g/hr in the reactor with a resulting molar feed ratio of isoflurane:HF of 1:1.9. The reaction temperature was maintained at 153° C. in the reactor. The reaction was allowed to stabilise for 2 hours. The reaction was then run for further 6 hours.

The total feed after the period of stabilisation was found to be isoflurane, 133.7 g (0.725 m) and anhydrous hydrogen fluoride, 27.3 g (1.37 m). The desflurane product was condensed and neutralised as described above. The final combined product was analyzed as desflurane 57.4%, isoflurane 42.0%, desflurane compound A (($CF_3CHF)_2O$) USP April 2005) 0.1% and a volatile fragmentation by-product 0.1%. The weight of the recovered crude products was 112 g. The reaction yield of desflurane was thus 52.8% with a conversion efficiency of 64.8% and an overall selectivity to desflurane of 81.5%.

Example 2

The fluorination catalyst was prepared, charged, conditioned and heated to the reaction temperature (135° C.) as described above. The metal pentahalide used in this process was antimony pentafluoride in molar equivalents of 1.5 mmol/g. The supporting substrate employed was activated carbon. The pressure of the system was 0-0.2 bar.

Isoflurane was fed continuously as a vapour at a rate of 16 g/hr and anhydrous HF vapour was fed at a rate of 5.0 g/hr to the reactor with a resulting molar feed ratio of isoflurane:HF of 1:2.8. The reaction temperature was maintained at 135° C. in the reactor. The desflurane product was condensed and neutralized as described above and routinely sampled and analysed. The reaction was then continued to run for 110 hours. The analysis after 10 hours of stabilisation indicated 80% to 83% desflurane product recovered with most of the balance being isoflurane. The final bulk product after drying with sodium sulphate, was analyzed as desflurane 81.9%, isoflurane 17.8%, desflurane compound A (($CF_3CHF)_2O$) USP April 2005) 0.06% and 0.3% volatile fragmentation by-products.

The total feed after the period of stabilisation was isoflurane 1595 g (8.645 m) and anhydrous hydrogen fluoride 488 g (24.40 m). The weight of crude products recovered was 1296 g. The reaction yield of desflurane was thus 73.1% with a conversion efficiency of 85.5% and an overall selectivity of 85.5% to desflurane.

DEFINITIONS

The following terms shall have, for the purposes of this application, respective meanings set forth below.

Reaction yield shall mean:

$$\frac{\text{Moles of desflurane obtained}}{\text{Moles of reactant feed charged}} \times 100$$

Conversion efficiency shall mean:

$$\frac{\left(\begin{array}{c}\text{Moles of reactant feed charged} - \\ \text{Moles of reactant out}\end{array}\right)}{\text{Moles of reactant feed charged}} \times 100$$

$$\text{Selectivity \%} = \frac{\text{(Moles of desflurane obtained)}}{\left(\begin{array}{c}\text{Moles of reactant feed charged} - \\ \text{Moles of reactant out}\end{array}\right)} \times 100$$

Hence, $$\text{Selectivity \%} = \frac{\text{Reaction Yield}}{\text{Conversion}} \times 100$$

We claim:

1. A process for the production of 1,2,2,2-tetrafluoroethyl difluoromethyl ether (desflurane), comprising:
    passing into a reactor a feed mixture consisting of 1-chloro-2,2,2-trifluoroethyl difluoromethyl ether (isoflurane) and anhydrous hydrogen fluoride in the vapour phase;
    the feed mixture being passed over a fluorination catalyst system consisting essentially of a metal pentahalide absorbed on a supporting substrate at a temperature ranging from 100° C. to 180° C;
    the process being operated as a continuous process.

2. The process as claimed in claim 1, wherein the said feed mixture consisting of anhydrous hydrogen fluoride (HF) and 1-chloro-2,2,2-trifluoroethyl difluoromethyl ether (isoflurane) has a molar ratio of HF to isoflurane in the range from 0.25:1 to 10:1.

3. The process as claimed in claim 1, wherein the said feed mixture consisting of anhydrous hydrogen fluoride (HF) and 1- chloro-2,2,2-trifluoroethyl difluoromethyl ether (isoflurane) has a molar ratio of HF to isoflurane in the range from 1:1 to 5:1.

4. The process as claimed in claim 1, wherein the said feed mixture consisting of anhydrous hydrogen fluoride (HF) and 1-chloro-2,2,2-trifluoroethyl difluoromethyl ether (isoflurane) has a molar ratio of HF to isoflurane in the range from 1.5:1 to 4:1.

5. The process as claimed in claim 1, wherein said feed mixture is passed over said fluorination catalyst system at a temperature ranging from 120° C. to 150° C.

6. The process as claimed in claim 1, wherein said metal pentahalide is selected from a group consisting of antimony pentachloride, antimony pentafluoride, arsenic pentafluoride, tantalum pentachloride and niobium pentafluoride, or mixtures thereof.

7. The process as claimed in claim 6, wherein said metal pentahalide is selected from antimony pentachloride, antimony pentafluoride, or mixtures thereof.

8. The process as claimed in claim 1, wherein the supporting substrate in the fluorination catalyst system is selected from carbon or alumina.

9. The process as claimed in claim 8, wherein said carbon is an activated carbon.

10. The process as claimed in claim 1, wherein in the fluorination catalyst system the concentration of said metal pentahalide on the said supporting substrate is 0.5 to 4.0 mmol/g.

11. The process as claimed in claim 10, wherein the concentration of said metal pentahalide on the said supporting substrate is from 0.5 to 2.5 mmol/g.

12. The process as claimed in claim 10, wherein the concentration of said metal pentahalide on the said supporting substrate is from 1.0 to 2.0 mmol/g.

13. The process as claimed in claim 1, wherein passing of said feed mixture in the vapour phase over said fluorination catalyst system is carried out at an atmospheric pressure or an elevated pressure or a reduced pressure within the range from 0.5 to 10 bar.

14. The process as claimed in claim 13, wherein passing of said feed mixture in the vapour phase over said fluorination catalyst system is carried out at an atmospheric pressure or an elevated pressure or a reduced pressure within the range from 0.8 to 4 bar.

* * * * *